United States Patent [19]

Pondebat et al.

[11] Patent Number: 5,817,889

[45] Date of Patent: *Oct. 6, 1998

[54] PROCESS FOR THE PURIFICATION OF A GLYCOL SOLUTION

[75] Inventors: Chantal Pondebat; Claude Blanc, both of Pau; Daniel Morin, Orthez, all of France

[73] Assignee: Elf Aquitaine Production, Courbevoie, France

[ * ] Notice: This patent issued on a continued prosecution application filed under 37 CFR 1.53(d), and is subject to the twenty year patent term provisions of 35 U.S.C. 154(a)(2).

[21] Appl. No.: 464,720

[22] PCT Filed: Oct. 27, 1994

[86] PCT No.: PCT/FR94/01249

§ 371 Date: Aug. 7, 1995

§ 102(e) Date: Aug. 7, 1995

[87] PCT Pub. No.: WO95/11876

PCT Pub. Date: May 4, 1995

[30] Foreign Application Priority Data

Oct. 29, 1993 [FR] France ................................. 93 12914

[51] Int. Cl.$^6$ ................................................... B01D 15/00

[52] U.S. Cl. ............................ 568/679; 568/680; 568/868

[58] Field of Search ..................................... 568/679, 680, 568/868

[56] References Cited

U.S. PATENT DOCUMENTS 4,518,396   5/1985   Rawson ................................. 48/196 R

FOREIGN PATENT DOCUMENTS 089704   9/1983   European Pat. Off. .
2823177  5/1978   Germany .

*Primary Examiner*—Brian M. Burn
*Assistant Examiner*—S. Padmanabhan
*Attorney, Agent, or Firm*—Burgess, Ryan & Wayne

[57] ABSTRACT

An amount of water is added to a glycol solution to be purified to enable segregation of the resulting mixture into a hydrocarbon phase and a glycol phase. The hydrocarbon phase is separated from the glycol phase and said glycol phase is desalted, e.g. by electrodialysis, to give a desalted and substantially hydrocarbon-free glycol solution which is then concentrated by steam stripping. The method is useful for purifying waste glycol solutions resulting from oil or gas production effluent processing using glycols, and in particular from a gas hydrate inhibition treatment or natural gas dehydration.

22 Claims, 2 Drawing Sheets

PROCESS FOR THE PURIFICATION OF A GLYCOL SOLUTION

This is the U.S. National Stage Application of PCT/FR94/01249 filed Oct. 27, 1994, now WO95/11876 published May 4, 1995.

The invention relates to a process for the purification of a glycol solution based on one or more glycols and additionally containing water and, as impurities, dissolved salts and hydrocarbons in the dissolved and/or emulsified state. The invention relates, in particular, to the regeneration of glycol solutions of the abovementioned type, which are formed during various treatments of effluents of gas or petroleum production by glycols, especially dehydration treatment of natural gases or alternatively, treatment for prevention of the formation of gas hydrates, particularly, hydrates of natural gases or of petroleum gas, in the discharge pipes of the multiphase effluents from petroleum or gas production.

The glycols used for the treatment of the effluents of petroleum or gas production are diols, in which the OH groups are located at the end of the molecular chain and which are included in the general formula $HO-(C_nH_{2n}O)_p-C_nH_{2n}OH$, in which n is an integer ranging from 2 to 4, preferably equal to 2 or 3, and p represents 0 or an integer ranging from 1 to 4, preferably 0 or an integer equal to 1 or 2.

Three glycols corresponding to the abovementioned formula are widely used in the petroleum and gas industry and in particular in the field of the production of natural gas. These are monoethylene glycol (MEG) of formula $HOCH_2CH_2OH$ (n=2 and p=0 in the general formula), diethylene glycol (DEG) of formula $HOCH_2CH_2OCH_2CH_2OH$ (n=2 and p=1 in the general formula) and triethylene glycol (TEG) of formula $HOCH_2CH_2OCH_2CH_2OCH_2CH_2OH$ (n=2 and p=2 in the general formula).

Glycols such as MEG, DEG and TEG are used to prevent the formation of gas hydrates in pipes serving to discharge the multiphase effluents arising from sites for petroleum or gas production. The hydrates are solid products, which are formed by association of molecules of water and gas, especially natural gas or petroleum gas, under certain temperature and pressure conditions. These solid products may damage the pipes in which the petroleum or gas effluents circulate or may prevent the discharge of the said effluents by plugging the pipes. Injection of MEG, DEG or TEG into the said pipes has the effect of displacing the pressure and temperature conditions for formation of the hydrates to values which are sufficiently different from the pressure and temperature conditions prevailing in the pipes, in order to allow the petroleum or gas effluents in these pipes to flow without incident. These glycols are separated from the petroleum or gas effluents containing them and are regenerated in plants located at the terminal for reception of the said effluents. Regeneration is carried out by a well known stripping technique using steam and optionally an extra gas, this stripping generally being carried out in a regeneration column equipped with a boiler including a system of indirect heat exchange containing tubes or plates through which a heat exchange fluid circulates.

The implementation of regeneration of the glycol which is recovered, in the form of a mixture with water, at the terminal for reception of the petroleum or gas effluents comes up against difficulties of two types.

Firstly, it often arises that deposit water plugs containing high levels of salts, for example alkali metal or alkaline-earth metal chlorides and sulphates such as NaCl, KCl, $Na_2SO_4$, $CaCl_2$, $MgCl_2$, $BaCl_2$ and $SrCl_2$, are extracted from the deposit with the gas and the liquid hydrocarbons produced by the deposit. The water contained in the petroleum or gas effluent, which forms by condensation of steam in the discharge pipe, mixes with this deposit water to such an extent that it is necessary, at the terminal, to regenerate a mixture of glycol and salt water. If the salt content exceeds a certain threshold, the salts are deposited in the hottest part of the stripping regeneration column. They form a crust in particular on the tubes or plates of the heat exchanger of the regeneration column boiler, thereby preventing good heat transfer and likewise inducing problems of corrosion and of piercing of the tubes or plates of the heat exchanger.

Furthermore, the glycols injected into the discharge pipes of the petroleum or gas multiphase effluents arising from the production deposits are in contact with liquid hydrocarbons which contain, in particular, aromatic constituents, for which the glycols have great affinity. If no treatment of the glycol is made before regeneration, these hydrocarbons dissolved by the glycol will be stripped out with the water during the regeneration, resulting in the emission of toxic fumes which are discharged into the atmosphere.

Glycols such as TEG and DEG are used to dehydrate natural gases on land or on platforms at sea. The wet natural gas is washed with the glycol in an absorption tower in order to dry the gas and the used glycol charged with water is subjected to a regeneration by stripping in a regeneration column equipped with a boiler including, as in the above case, a system of indirect heat exchange containing tubes or plates through which a heat exchange fluid circulates.

While regeneration of the used glycol arising from the absorption tower is being carried out, there are encountered difficulties similar to those encountered during regeneration of the glycols arising from the treatment for prevention of the formation of gas hydrates in the discharge pipes of the petroleum or gas multiphase effluents. Indeed, on the one hand, since the glycol has a strong affinity for the aromatic hydrocarbons, it absorbs, at the same time as the water, the vapours of these hydrocarbons which are present in the natural gas to be dried. These hydrocarbons are stripped out and discharged into the atmosphere during regeneration of the used glycol, giving rise to the same toxic emissions as those mentioned in the above case. Moreover, it often arises that, despite the presence of round-bottomed separating vessels arranged upstream of the dehydration plant, salt water deposit plugs penetrate into the absorption tower with the gas to be dried. The salts carried by this salt water are found in the used glycol subjected to the regeneration and are deposited on the tubes or plates of the heat exchanger of the regeneration column boiler, thereby giving rise to an energy loss and corrosion phenomena leading to piercing of these tubes or plates.

Citations U.S. Pat. No. 4,427,567 and SU-A-850,181 propose processes for regeneration of glycol solutions containing one or more glycols, water and dissolved salts, the said processes consisting in subjecting the said glycol solutions to a treatment for separation of the salts by electrodialysis using membranes which are selectively permeable to cations and membranes which are selectively permeable to anions, and then in removing some of the water contained in the desalted glycol solution by steam stripping in order to obtain a purified glycol solution with a higher concentration of glycols.

Application of such procedures to the purification of glycol solutions containing, as impurities, not only dissolved salts but also hydrocarbons, poses serious implementation problems. Indeed, the presence of hydrocarbons, especially if they are very heavy (hydrocarbons containing more than 12 carbon atoms), in the glycol solution to be regenerated or purified leads to relatively rapid clogging of the selective permeable membranes used in the treatment for separation of the salts by electrodialysis (desalting treatment), owing to the deposition of these hydrocarbons at the surface of the said membranes, with the consequence that the plant using the said desalting treatment can function acceptably only for a limited period, thereby excluding the possibility of using the desalting treatment continuously.

The invention proposes a process for the purification (regeneration) of glycol solutions based on one or more glycols and containing water and, as impurities, dissolved salts, which are dissociated as anions and cations, and hydrocarbons in the dissolved and/or emulsified state, which is of the type in which the glycol solution is subjected to a desalting treatment using a technique for the selective separation of the anions and cations of the dissolved salts, and which, in order to overcome the abovementioned drawbacks associated with the presence of hydrocarbons in the glycol solution, includes, according to the invention, a specific step for the separation of the said hydrocarbons before subjecting the glycol solution to the desalting treatment.

The process according to the invention makes it possible to produce a purified glycol solution, which is substantially free of salts and hydrocarbons, under conditions which allow the purification to be carried out continuously over periods which are compatible with industrial exploitation. Furthermore, when the treatment for elimination of the salts makes use of a membrane technique using membranes having selective permeability to ions, implementation of the purification as proposed by the invention makes it possible to increase considerably the lifetime of the separation membranes. Furthermore, when the membrane separation technique is an electrodialysis, this implementation also makes it possible to reduce the electrical power necessary to operate the electrodialysis plant.

The process according to the invention for the purification of glycol solutions based on one or more glycols and containing water and, as impurities, dissolved salts, which are dissociated as anions and cations, and hydrocarbons in the dissolved and/or emulsified state, is of the type including a treatment for elimination of the salts dissolved in the glycol solution, referred to as a desalting treatment, using a technique for the selective separation of the anions and cations of the said salts, and it is characterized in that there is first incorporated into the glycol solution to be purified an amount of water which allows demixing of the resulting mixture into a hydrocarbon phase, consisting of virtually all of the hydrocarbons present in the glycol solution to be purified, and into a glycol phase, formed of the other constituents of the glycol solution and the added water, the glycol phase is separated from the hydrocarbon phase and the said glycol phase is subjected to the desalting treatment, with production of a purified glycol solution having a low hydrocarbon content and a controlled salt content.

The purified glycol solution arising from the desalting treatment is advantageously subjected to concentration by stripping using steam and optionally an extra gas, so as to bring the water content of the said solution to a desired value which is compatible, for example, with the content required for reutilization of the solution in a treatment for drying natural gases or in a treatment for inhibiting the formation of gas hydrates in the discharge pipes of the petroleum or gas multiphase effluents.

The glycol or the glycols present in the glycol solution to be purified by the process according to the invention are, in most cases, those which are included in the general formula HO—$(C_nH_{2n}O)_p$—$C_nH_{2n}OH$ defined above, and advantageously have less than seven carbon atoms in the molecule, the most common glycols being those such as MEG, DEG, TEG and propylene glycol.

The hydrocarbons contained in the glycol solution to be purified are generally hydrocarbons having more than five carbon atoms in the molecule, especially $C_6$ to $C_{20}$ hydrocarbons, which may be aromatic hydrocarbons such as, for example, benzene, toluene, ethylbenzene and xylenes, naphthenic hydrocarbons and, to a lesser extent, aliphatic hydrocarbons, for example alkanes, and cycloaliphatic hydrocarbons, as well as mixtures of such hydrocarbons. These hydrocarbons, the overall content of which in the glycol solution is less than 20% by weight in the majority of cases, are present in the said solution in the dissolved state and/or as a suspension of fine droplets which may or may not be of the emulsion type.

The salts, which are present in the glycol solution to be purified and which are removed by the desalting treatment, are more particularly inorganic salts, especially alkali metal or alkaline-earth metal chlorides and sulphates such as, for example, NaCl, KCl, $Na_2SO_4$, $MgSO_4$, $CaCl_2$, $BaCl_2$, $SrCl_2$ and $MgCl_2$, the concentration of which in the glycol solution is less than the saturation concentration. The said salts are thus fully soluble in the glycol solution and are thus dissociated as anions and cations in this solution.

The amount of water which is added to the glycol solution to be purified, in order to obtain demixing of the mixture into the hydrocarbon phase and the glycol phase, is advantageously such that the quotient $\alpha$ of the water:hydrocarbons volume ratio, in the glycol solution after addition of the water required for demixing, to the water:hydrocarbons volume ratio, in the glycol solution to be purified before addition of the water for demixing, is between 1 and 15 and more particularly between 1 and 10. More especially, when the glycol solution to be purified is based on MEG and/or DEG, $\alpha$ is preferably such that $1<\alpha<2$, whereas for a glycol solution based on TEG, $\alpha$ is preferably such that $5<\alpha<10$.

The steps of addition of water to the glycol solution to be purified, resulting in demixing of the resulting mixture into the hydrocarbon phase and the glycol phase, and of separation of the said phases from each other are performed at pressures corresponding substantially to atmospheric pressure, pressure losses aside, and at temperatures generally below about 60° C. and more particularly ranging from 5° C. to 50° C.

The glycol phase arising from the demixing is advantageously subjected to a filtration before being brought to the desalting treatment, in order to remove solid particles which may be present in the said phase, the mean diameter of which particles is greater than about 10 $\mu$m.

As mentioned above, desalting of the substantially hydrocarbon-free glycol phase may be performed using any technique which makes it possible to carry out a selective separation of the cations and the anions arising from the salts dissolved in the said glycol phase. It is possible, for example, to use an ion exchange technique consisting in percolating the glycol solution to be desalted through one or more beds of ion exchange materials, especially ion exchange resins, which selectively bind the anions, and ion exchange materials, especially ion exchange resins or alternatively zeolites, which selectively bind the cations.

Desalting of the glycol phase is advantageously performed by electrodialysis, that is to say by a technique involving the transfer, under the effect of a continuous electric field, of the anions and cations present in the glycol solution to be desalted, through membranes which are selectively permeable to anions and membranes which are selectively permeable to cations respectively. In order to carry out the electrodialysis operation, use may be made of the various known electrodialysis machines, which all contain a positive electrode (anode) and a negative electrode (cathode) between which membranes which are alternately selectively permeable to anions and to cations are arranged such that a space or compartment is provided between each electrode and the membrane opposite it and also between each successive pair of membranes and such that the membrane opposite the anode or respectively the cathode is a membrane which is selectively permeable to cations.

The electrodialysis machine is thus in the form of a series of compartments referred to as concentration compartments and of compartments referred to as dilution compartments. The dilution compartments are connected in parallel, via one end, to a pipe for supplying the solution to be desalted and, via an opposite end, to a pipe for discharging the desalted solution. The concentration compartments are connected in parallel, via one end, to a pipe for supplying a washing liquid, generally water, and, via an opposite end, to a pipe for discharging a salt solution (brine). The electrodialysis machine also includes means for allowing the compartments to be maintained at the temperature required for the operation and a DC voltage generator which applies the desired DC voltage between the electrodes in order to produce the DC electric current for the electrodialysis. Detailed information on how to carry out the electrodialysis operation and especially on the choice of membranes which are selectively permeable to anions (anionic membranes) or respectively to cations (cationic membranes) are given in the monograph by Andre Bonnin entitled "Electrodialysis" and published in Techniques de L'Ingenieur, part J 2840. To this monograph, there may also be added the monograph by Wayne A. McRae entitled "Electrodialysis" and published in the Kirk-Othmer Encyclopedia, Encyclopedia of Chemical Technology, Third Edition (1978), Volume 8, pages 726 to 738, as well as the content of the citations U.S. Pat. No. 4,427,507 and SU-A-850,181. The teaching provided by these various documents is incorporated by reference in the present description.

The operating conditions to perform the electrodialysis, in particular the intensity of the current flowing between the electrodes, the salt concentration in the glycol phase and the duration of the electrodialysis treatment, are adjusted, as is known in the art, in order to obtain the desired degree of desalting while at the same time limiting the losses of glycol resulting from the passage of glycol through the membranes.

When the electrodialysis is carried out continuously, the application of a constant DC voltage between the electrodes of the electrodialysis machine is reflected by a DC current of substantially constant intensity I flowing between the said electrodes. On the other hand, when the electrodialysis is performed discontinuously, the application of a constant DC voltage between the electrodes of the electrodialysis machine is reflected by a DC current, flowing between the said electrodes, the intensity i of which decreases when the duration of the electrodialysis increases. It is possible, however, to arrive at the notion of constant intensity of the above case by defining an imaginary, mean constant intensity Im which would lead, over the same treatment period, to the same desalting performances as the intensity i. Advantageously, when the electrodialysis is carried out, a current density, that is to say a ratio between the intensity i or Im to the surface area occupied by a membrane, of between 0.1 and 450 $A/m^2$ is set.

More particularly, when the glycol phase to be desalted contains glycol consisting respectively of MEG, DEG and TEG, a current density of between 0.1 and 150 $A/m^2$, 0.1 and 300 $A/m^2$ and 0.1 and 450 $A/m^2$ respectively is set for the electrodialysis.

As mentioned above, the desalted glycol solution arising from the desalting operation may be subjected to concentration by stripping using steam and optionally an intermediary stripping gas. This concentration is performed, in a manner which is known per se, in a stripping column provided with gas/liquid contact plates or an equivalent height of a suitable packing. The stripping column operates with a head pressure generally ranging from 1 to 3 bar absolute and a temperature at the foot of the column chosen such that the water content of the concentrated purified glycol solution is reduced to the desired value.

The process according to the invention is most particularly applicable to the purification (regeneration) of used glycol solutions collected during the treatment of petroleum or gas production effluents by glycols. The said process is most especially suitable for the purification of used glycol solutions arising from the dehydration treatment of natural gases by glycols or alternatively from the treatment, by glycols, for prevention of the formation of gas hydrates, especially hydrates of natural gases or of petroleum gas, in the discharge pipes of multiphase effluents from petroleum or gas production.

BRIEF DESCRIPTION OF THE FIGURES

Other characteristics and advantages of the invention will emerge on reading the following description of two of the embodiments thereof which are given with reference to the attached diagram, in which.

Figure 1:
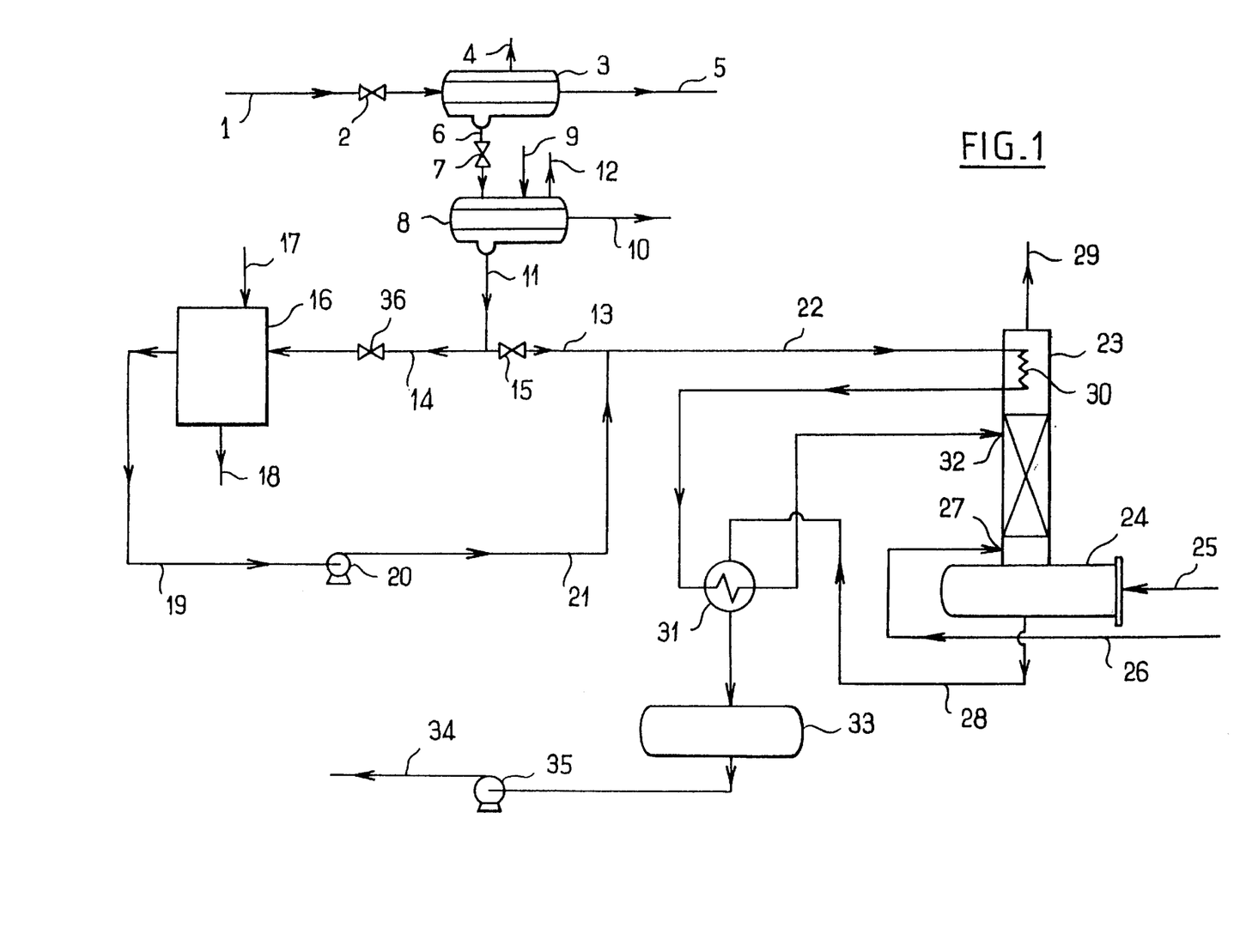
FIG. 1 schematically represents a plant for allowing the regeneration of a used glycol solution arising from the treatment, by a glycol (MEG, DEG or TEG), for inhibition of the formation of gas hydrates, which plant includes a purification treatment according to the invention.

With reference to FIG. 1, the used glycol is solution, which arises from the treatment for inhibition of the formation of gas hydrates and contains a glycol, water, salts, liquid hydrocarbons and gaseous hydrocarbons, arrives under a pressure of a few bars via a pipe 1 and, after passing through a valve 2, enters into a round-bottomed phase separation vessel 3. Inside the round-bottomed vessel 3, the used glycol solution undergoes a decompression, to a pressure equal to atmospheric pressure or in the region of this pressure, and thereby separates into three fractions, namely an upper gaseous fraction, consisting of natural gas and discharged via a pipe 4, an intermediate fraction, consisting of some of the liquid hydrocarbons present in the used glycol solution arriving via the pipe 1, which intermediate fraction is discharged via a pipe 5, and a lower liquid fraction, discharged via a pipe 6, through a valve 7, and containing the glycol, the water and the salts present in the used glycol solution arriving via the pipe 1 as well as the liquid hydrocarbons arising from the said glycol solution and which have not passed to the intermediate fraction, the said lower liquid fraction constituting a glycol solution, to which is applied the purification according to the invention. In this glycol solution, the hydrocarbons are in dissolved form and also in the form of fine droplets as a suspension in the mixture of salt water and glycol.

The glycol solution to be purified circulating in the pipe 6 is introduced into a round-bottomed phase separation vessel 8, into which is also injected, via a tube 9, an amount of water which is suitable to demix the resulting mixture into an upper liquid phase, discharged via a pipe 10 and consisting of most of the liquid hydrocarbons present in the glycol solution entering the separator 8, and into a lower liquid phase, referred to as the glycol phase, discharged via a pipe 11, which glycol phase is substantially free of hydrocarbons and contains the glycol, the water and the salts present in the glycol solution entering the separator 8 as well as the water introduced via the tube 9. The gaseous hydrocarbons possibly present in the glycol solution entering the separator 8 are discharged via a pipe 12 placed in the upper part of the said separator.

The glycol phase arising from the separator 8, via the pipe 11, is divided into a first stream 13 and a second stream 14, the ratio of the flow rates of which is controllable, by actuating valves 15 and 36 of adjustable opening, the said stream 14 being led, through valve 36, to a desalting unit 16 consisting of an electrodialysis machine equipped with membranes which are selectively permeable to anions or respectively to cations, these membranes being arranged between two electrodes as mentioned above and organized schematically, in particular, in the monograph by Andre Bonnin. The flow rate of the glycol solution led to the electrodialysis machine may vary within a wide range depending on the treatment units and events for exploitation of the hydrocarbon deposit providing the multiphase effluents treated by the glycols. The said flow rate may be up to 100% of the flow rate of the glycol phase passing through the pipe 11 in the case of a sudden arrival of a large amount of salts in the petroleum effluent treated by glycol or, on the contrary, may be limited to a few per cent, for example 2 to 10%, of the glycol phase flow rate if this phase is not heavily laden with salt. The electrodialysis machine 16 produces, on the one hand, a brine, discharged via a pipe 18 and consisting of a concentrated solution of the salts separated from the glycol phase, and, on the other hand, a purified glycol solution, discharged via a pipe 19 and consisting of a mixture of glycol and water substantially free of hydrocarbons and salts. The electrodialysis machine is fitted, at its inlet, with a water injection tube 17 which makes it possible to adjust, by dilution, the concentration of salts in the brine. The brine discharged via the pipe 18 may be reintroduced into the ground, via a well provided for this purpose, or may be discharged into the sea or alternatively may be incinerated.

The purified glycol solution leaving the electrodialysis machine 16, via the pipe 19, is introduced via a pipe 21, on which is mounted a pump 20, into the stream 13 of non-desalted glycol phase in order to form a stream 22, which is concentrated in a stripping column 23 using as stripping agent, on the one hand, steam produced by a boiler 24 associated with the column, the said boiler being heated, for example, by combustion of a combustible gas conveyed via a pipe 25, and, on the other hand, an intermediary stripping gas arriving via a pipe 26 and opening, at an inlet 27, into the lower part of the column 23. The operation of concentration by stripping in the column 23 produces a purified and concentrated glycol solution, which is discharged from the bottom of the column 23 via a pipe 28, and a stream of steam and stripping gas, discharged from the head of the column 23 via a pipe 29. The stream 22 of glycol solution to be concentrated is first heated, by a first indirect heat exchange 30 with the content of the upper part of the column 23, and then by a second indirect heat exchange 31 with the purified and concentrated glycol solution passing through the pipe 28, before being injected into the stripping column 23, via an inlet 32 located between the level of the first heat exchange 30 and the level of the inlet 27 for the stripping gas.

After the phase of heat exchange 30 with the stream 22 of glycol solution to be concentrated, the purified and concentrated glycol solution is led to a storage reservoir 33, from where it is recycled, via a pipe 34, equipped with a pump 35, to the site of use.

It is also possible to envisage functioning of the plant for which continuous demixing is carried out in the separator 8 and continuous concentration is carried out in the stripping column 23 and intermittent desalting is performed. To do this, the plant is first made to operate with the valve 15 completely open and the valve 36 completely closed, thus short-circuiting the desalting unit, and then at chosen time intervals the valve 15 is completely closed and the valve 36 is opened fully and this situation is maintained until the regenerated glycol solution arriving at the storage vat is desalted to the appropriate salt content, after which the starting operating conditions are readopted; valve 15 completely open and valve 36 fully closed.

Figure 2:
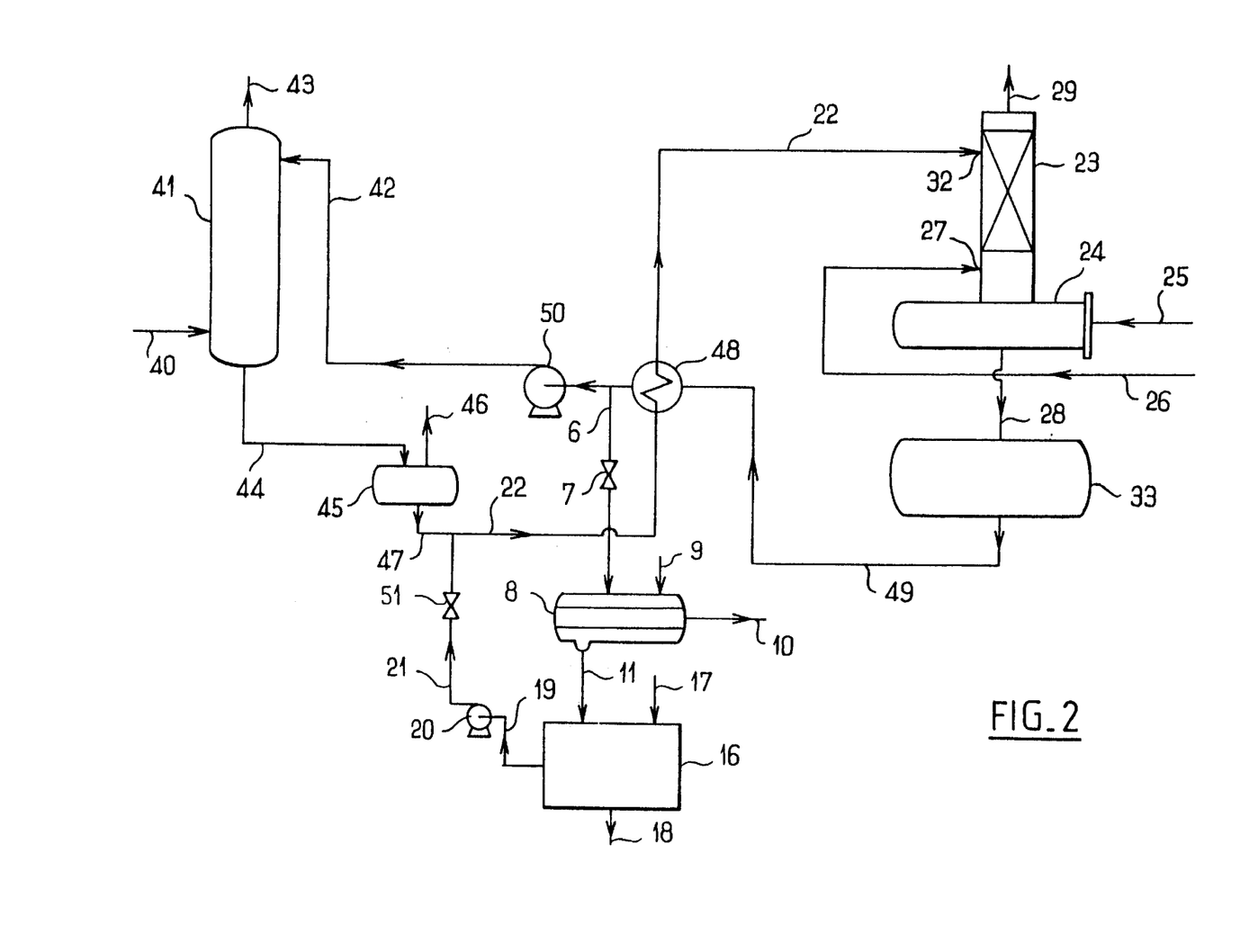
FIG. 2 schematically represents a plant for allowing the regeneration of a used glycol solution arising from a treatment for dehydration of a natural gas by a glycol (TEG or DEG).

With reference to FIG. 2, a wet natural gas to be dehydrated, occasionally containing water plugs containing dissolved salts, is injected, via a pipe 40, into the lower part of an absorption column 41, equipped with a gas/liquid contact system, and meets in this column, in countercurrent, a regenerated glycol solution consisting of glycol, for example TEG or DEG, which is substantially anhydrous, and which is injected, via a pipe 42, into the upper part of the column 41. A dehydrated natural gas is discharged via a pipe 43, mounted at the head of the column 41, whereas a used glycol solution containing the glycol injected into the column 41, as well as the water, the salts and the hydrocarbons derived from the natural gas placed in contact with the glycol, is withdrawn from the foot of the said column, via a pipe 44. The used glycol solution enters a round-bottomed pressure-release vessel 45, in which it undergoes decompression to a pressure substantially equal to atmospheric pressure, resulting in the formation of a gaseous fraction, consisting of natural gas and discharged via a pipe 46 from the head of the round-bottomed vessel 45, and a liquid fraction withdrawn via a pipe 47 from the bottom of the round-bottomed vessel 45 and consisting of glycol, water and liquid hydrocarbons.

The said liquid fraction forms the main component of a glycol liquid stream 22 which, after heating in an indirect heat exchanger 48, is concentrated in a stripping column 23 using as stripping agent, on the one hand, steam produced by a boiler 24 associated with the column 23, the said boiler being heated, for example, by combustion of a combustible gas conveyed via a pipe 25, and, on the other hand, an intermediary stripping gas arriving via a pipe 26 and opening, via an outlet 27, into the lower part of the column 23. The operation of concentration by stripping in the column 23 produces a concentrated glycol solution, which is discharged from the foot of the column 23 via a pipe 28, and a stream of steam and stripping gas, discharged from the head of the column 23 via a pipe 29.

The concentrated glycol solution withdrawn from the column 23 via the pipe 28 is conveyed to a storage reservoir 33, from which it is recirculated to the absorption column 41, through a pipe 49, on which is mounted the hot circuit of the heat exchanger 48, a pump 50 and the pipe 42. During its passage through the heat exchanger 48, the concentrated glycol solution arising from the storage reservoir 33 loses its heat energy to the glycol stream 22 conveyed to the stripping column 23, thereby providing heating of the said stream 22.

The concentrated glycol solution recycled to the absorption column 41 contains the non-strippable hydrocarbons and the salts contained in the glycol liquid stream 22 conveyed to the stripping column 23.

By working continuously or else at determined time intervals, a fraction of variable flow rate of the concentrated glycol solution circulating in the pipe 49, between the heat exchanger 48 and the pump 50, is withdrawn, via the pipe 6 equipped with a valve 7 of adjustable opening, in order to subject the said fraction to a purification according to the invention.

The glycol solution to be purified passing through the pipe 6 is introduced into a round-bottomed phase separation vessel 8, in which is also injected, via a tube 9, an amount of water suitable to induce demixing of the resulting mixture into an upper liquid phase, discharged via a pipe 10 and consisting of virtually all of the liquid hydrocarbons present in the glycol solution entering the separator 8, and of a lower liquid phase, referred to as the glycol phase, discharged via a pipe 11, which glycol phase is substantially free of hydrocarbons and contains the glycol, the water and the salts present in the glycol solution entering the separator 8 as well as the water introduced via the tube 9.

The glycol phase arising from the separator 8, via the pipe 11, is introduced into a desalting unit 16 consisting of an electrodialysis machine of structure comparable to that used in the plant of FIG. 1. The electrodialysis machine 16 produces, on the one hand, a brine, discharged via a pipe 18 and consisting of a more or less concentrated solution of the salts separated from the glycol phase, and, on the other hand, a purified glycol solution, discharged via a pipe 19 and consisting of a mixture of glycol and water substantially free of hydrocarbons and salts. The electrodialysis machine is fitted, at its inlet, with a water injection tube 17 which allows the concentration of salts in the brine to be adjusted by dilution. The brine discharged via the pipe 18 may then be treated as mentioned in the case of the plant of FIG. 1.

The purified glycol solution leaving the electrodialysis machine 16, via the pipe 19, is introduced, via a pipe 21, on which are mounted a pump 20 and then a valve 51 of adjustable opening, into the liquid fraction withdrawn from the foot of the round-bottomed vessel 45 via the pipe 47, in order to constitute the glycol liquid stream 22 which is concentrated in the stripping column 23.

During the treatment for dehydration of a natural gas by a glycol, it is observed that the more the glycol absorbs heavy hydrocarbons, the greater is the co-absorption of light aromatic hydrocarbons. Besides the fact that it improves the performances of the desalting unit, the separation of the heavy hydrocarbons contained in the glycol solution to be purified before the desalting operation allows the content of heavy hydrocarbons to be reduced in the regenerated glycol solution recycled to the absorption column, in which the natural gas is dehydrated by the glycol, with a consequent decrease in the co-absorption of aromatic hydrocarbons by the glycol and thus a concomitant reduction in the emissions of light aromatic hydrocarbons in the stream of steam and stripping gas discharged from the head of the stripping column. Moreover, the absorption of hydrocarbons by the glycol, whether these are heavy hydrocarbons or lighter ones such as aromatic hydrocarbons, is reflected by a decrease in the absorbing power of the glycol with respect to water. In order to obtain the same quality of dehydration of the natural gas, it is thus necessary to increase the flow rate of glycol in circulation, with a consequent increase in the energy consumption for regeneration of used glycol solution in the stripping column. The separation, proposed according to the invention, of the heavy hydrocarbons, contained in the glycol solution to be purified, before the desalting operation makes it possible to overcome this drawback.

In order to complete the description of the process according to the invention, which has just been presented, concrete examples of implementation of this process are given below, in a non-limiting manner.

EXAMPLES 1–2

A used glycol solution derived from the treatment for inhibition of the formation of natural gas hydrates was treated, by the purification process according to the invention, using MEG (Example 1) or DEG (Example 2) as hydrate inhibiting agent.

The glycol solution to be purified consisted of MEG (Example 1) or DEG (Example 2), water, salts (especially NaCl) and heavy hydrocarbons ($C_8$ hydrocarbons and greater), the said salts being in the dissolved state in the solution and the hydrocarbons partly in the dissolved state and partly in the emulsified state.

The purification was performed working continuously in a plant comparable to that described above with reference to FIG. 1 and operating as mentioned in this description.

The phase separator 8 operated at room temperature and at atmospheric pressure.

When carrying out Example 1, the valve 15 was closed and all of the flow rate of glycol phase leaving the separator 8 was introduced into the desalting unit, whereas in Example 2, the valve 15 was partially closed so as to introduce into the desalting unit 85% of the flow rate of glycol phase leaving the separator 8 via the pipe 11.

The desalting was performed using an electrodialysis machine marketed by the company Eurodia S.A., using membranes which are selectively permeable to anions or respectively to cations, these membranes being marketed by the company Tokuyama Soda under the names NEOSEPTA AM1® (anionic membranes) and NEOSEPTA CM1® (cationic membranes). The electrodialysis machine operated at a temperature in the region of room temperature, with a current density, defined as mentioned above, and at an electrical power which were respectively equal to 120 A/m$^2$ and 286 kW in Example 1 and 100 A/m$^2$ and 257 kW in Example 2.

The stripping column 23, used to concentrate the hydrocarbon-free and desalted glycol solution, operated at a head pressure equal to atmospheric pressure and with a boil temperature of about 120° C.

Table I below gives the flow rate and the composition of liquids flowing through various characteristic points of the plant.

The purified and concentrated glycol solution (regenerated solution), discharged via the pipe 34, contained no more hydrocarbons and had a salt content of 10 g/l in both examples, such a glycol solution being directly reusable in the treatment for inhibition of the formation gas hydrates.

The losses of glycol, in the desalting process by electrodialysis, were equal to 0.022 kg per hour and per m$^2$ of membrane in Example 1 and 0.019 kg per hour and per m$^2$ of membrane in Example 2;

TABLE I

| Example | Pipe from which the liquid is taken | Total flow rate of liquid (m³/h) | Glycol (t/h) | Water (t/h) | Heavy hydrocarbons (l/h) | Salts (kg/h) | Salt content (g/l) |
|---|---|---|---|---|---|---|---|
| 1 | 6  | 7.482 | 3.491  | 4.266 | 150 | 331.8  | 44.35  |
|   | 9  | 0.971 |        | 0.970 |     |        |        |
|   | 10 | 0.15  |        |       | 150 |        |        |
|   | 11 | 8.295 | 3.491  | 5.236 |     | 331.8  | 40     |
|   | 17 | 1.430 |        | 1.427 |     |        |        |
|   | 18 | 1.453 | 0.0255 | 1.427 |     | 285.98 | 196.85 |
|   | 19 | 8.271 | 3.465  | 5.236 |     | 45.83  | 5.54   |
|   | 22 | 8.271 | 3.465  | 5.236 |     | 45.83  | 5.54   |
|   | 29 | 3.746 |        | 3.740 |     |        |        |
|   | 34 | 4.583 | 3.491  | 1.496 |     | 45.53  | 10     |
| 2 | 6  | 7.123 | 4.059  | 3.458 | 150 | 302.63 | 42.49  |
|   | 9  | 0.602 |        | 0.601 |     |        |        |
|   | 10 | 0.15  |        |       | 150 |        |        |
|   | 11 | 7.566 | 4.059  | 4.059 |     | 302.63 | 40     |
|   | 17 | 1.286 |        | 1.284 |     |        |        |
|   | 18 | 1.303 | 0.0193 | 1.284 |     | 257.23 | 197.35 |
|   | 19 | 6.413 | 3.430  | 3.450 |     | >0.01  | ≈0     |
|   | 22 | 7.548 | 4.040  | 4.059 |     | 45.39  | 6.01   |
|   | 29 | 3.049 |        | 3.044 |     |        |        |
|   | 34 | 4.583 | 4.059  | 3.015 |     | 45.39  | 10     |

EXAMPLE 3

A used glycol solution resulting from the treatment for dehydration of a natural gas with TEG was subjected intermittently to a purification process according to the invention, working in a plant comparable to that described with reference to FIG. 2 and operating as mentioned in this description.

Schematically, a regenerated TEG solution was placed in contact, in countercurrent, in an absorption column 41 for the purpose of dehydrating natural gas with production of a used glycol solution withdrawn from the absorption column 41, via the pipe 44, and conveyed to the stripping column 23 for the purposes of regeneration, the regenerated glycol solution being recycled to the absorption column 41.

When the salt content of the regenerated glycol solution exceeded a predetermined threshold, the regenerated glycol solution was subjected to a purification until virtually complete desalting of the said solution was obtained. To do this, the purification circuit was connected by partially opening the valves 7 and 51 and the said circuit was kept in operating mode until the regenerated glycol solution, recycled to the absorption column 41, was fully desalted, after which the valves 7 and 51 were closed and the dehydration process was continued, a new purification according to the invention being performed when the salt content of the regenerated glycol solution again exceeded the predetermined threshold.

The phase separator 8 operated at room temperature and at atmospheric pressure.

During the purification treatment according to the invention, the degree of opening of the valves 7 and 51 was such that a flow rate of liquid representing about 3% of the flow rate conveyed, via the pipe 42, to the absorption column 41 was introduced into the separator 8. The valves 7 and 51 were reclosed after a period of 14 days.

The desalting was performed using an electrodialysis machine comparable to that used in Examples 1 and 2, the said electrodialysis machine operating at a temperature in the region of room temperature and with a mean current density, defined as indicated above, equal to 22 A/m² and at an electrical power of 600 W.

The stripping column 23 used to concentrate the used glycol solution operated at a pressure equal to atmospheric pressure and with a boil temperature of about 200° C.

The flow rate and the composition of liquids passing through various characteristic points of the plant are given in Table II.

The losses of glycol, in the desalting process by electrodialysis, were equal to 0.0169 kg per hour and per m² of membrane.

TABLE II

| Example | Pipe from which the liquid is taken | Total flow rate of liquid (m³/h) | TEG (t/h) | Water (kg/h) | Heavy hydrocarbons (l/h) | Salts (kg/h) | Salt content (g/l) |
|---|---|---|---|---|---|---|---|
| 3 | 44 (start) | 5.359   | 5.5526 | 292.2  | 150   | 20.6  | 3.844  |
|   | 9          | 0.01638 |        | 16.35  |       |       |        |
|   | 10         | 0.00446 |        |        | 4.464 |       |        |
|   | 11 (start) | 0.1641  | 0.1653 | 18.36  |       | 0.613 | 3.736  |
|   | 17         | 0.0030  |        | 3.06   |       |       |        |
|   | 19         | 0.1636  | 0.1647 | 18.36  |       | <0.01 | ≈0     |
|   | 18         | 0.0035  | 0.0005 | 3.06   |       | 0.613 | 173.88 |
|   | 22 (end)   | 5.372   | 5.717  | 310.6  |       | <0.01 | ≈0     |
|   | 29         | 0.2436  |        | 243.16 |       |       |        |
|   | 42 (end)   | 5       | 5.5526 | 67.44  |       | <0.01 | ≈0     |
|   | 6 (start)  | 0.1533  | 0.1653 | 2.01   | 4.464 | 0.613 | 4      |

TABLE II-continued

| Example | Pipe from which the liquid is taken | Total flow rate of liquid (m³/h) | TEG (t/h) | Water (kg/h) | Heavy hydrocarbons (l/h) | Salts (kg/h) | Salt content (g/l) |
|---|---|---|---|---|---|---|---| start = start of the desalting operation
end = end of the desalting operation

EXAMPLE 4

Working in a plant comparable to that described by way of reference to FIG. 1 and operating as indicated in this description, a used glycol solution, derived from the treatment for inhibition of the formation of natural gas hydrates using MEG as hydrate inhibitor, was subjected to a purification process according to the invention with continuous demixing being carried out in the separator 8 and continuous concentration being carried out in the stripping column 23 and intermittent desalting was performed when the salt content of the used glycol solution exceeded a determined threshold. The regenerated glycol solution was recycled continuously, via the pipe 34, for the treatment for inhibition of hydrates.

Part of the purification process was performed without desalting (valve 15 fully open and valve 36 completely closed). When the salt content of the used glycol solution exceeded a predetermined threshold, valve 15 was fully closed and valve 36 completely opened so as to bring all of the glycol phase arising from the separator 8 to the desalting unit, and the desalting unit was made to operate until the regenerated glycol solution discharged via the pipe 34 was desalted to the desired salt content. Thereafter, valve 36 was fully closed and valve 15 fully opened and desalting-free purification was continued a further desalting being performed when the salt content of the used glycol solution again exceeded the predetermined threshold.

The phase separator 8 operated at room temperature and at atmospheric pressure.

The desalting was performed using an electrodialysis machine comparable to that used in Examples 1 to 3, the said electrodialysis machine operating at a temperature in the region of room temperature, with a mean current density, defined as indicated above, equal to 120 A/m² and at an electrical power of 286 kW. Each desalting was performed over a period of 2.5 days, thereby allowing the salt content of the regenerated glycol solution to be brought to 10 g/l at the end of desalting.

The stripping column 23, used to concentrate the hydrocarbon-free and intermittently desalted glycol solution, operated at a head pressure equal to atmospheric pressure and with a boil temperature of about 120° C.

The flow rate and the composition of liquids passing through various characteristic points of the plant are given in Table III.

The losses of glycol, in the desalting process by electrodialysis, were equal to 0.022 kg per hour and per m² of membrane.

TABLE III

| Example | Pipe from which the liquid is taken | Total flow rate of liquid (m³/h) | MEG (t/h) | Water (kg/h) | Heavy hydrocarbons (l/h) | Salts (kg/h) | Salt content (g/l) |
|---|---|---|---|---|---|---|---|
| 4 | 6 (start) | 7.482 | 3.4907 | 4.266 | 150 | 331.81 | 44.35 |
|  | 9 | 0.971 |  | 0.971 |  |  |  |
|  | 10 | 0.15 |  |  | 150 |  |  |
|  | 11 (start) | 8.295 | 3.4907 | 5.236 |  | 331.81 | 40 |
|  | 14 (start) | 8.295 | 3.4907 | 5.236 |  | 331.81 | 40 |
|  | 17 | 1.430 |  | 1.427 |  |  |  |
|  | 18 | 1.453 | 0.0255 | 1.427 |  | 285.98 | 196.85 |
|  | 19 | 8.271 | 3.4652 | 5.236 |  | 45.83 | 5.541 |
|  | 22 | 8.271 | 3.4652 | 5.236 |  | 45.83 | 5.541 |
|  | 29 | 3.746 |  | 3.740 |  |  |  |
|  | 10 (end) | 4.583 | 3.4907 | 1.496 |  | 45.83 | 10 | start = start of the desalting operation
end = end of the desalting operation

We claim:

1. A process for the purification of glycol solutions based on one or more glycols and containing water and, as impurities, dissolved salts, which are dissociated as anions and cations, and hydrocarbons in at least one of the dissolved and emulsified states, said process consisting essentially of
   a) incorporating into the glycol solution to be purified an amount of water which allows demixing of the resulting mixture into a hydrocarbon phase consisting of virtually all of the hydrocarbons present in said glycol solution to be purified, and into a glycol phase, formed of the other constituents of the glycol solution and the added water;
   b) separating the glycol phase from the hydrocarbon phase; and
   c) subjecting the separated glycol phase to a desalting treatment for elimination of the salts dissolved in said glycol phase by making use of a technique for the selective separation of the anions and cations of said salts, with production of a purified glycol solution having a low hydrocarbon content and a controlled salt content.

2. A process according to claim 1, wherein the glycol solution to be purified contains a hydrocarbon content of less than 20% by weight.

3. A process according to claim 1, wherein the glycol or glycols present in the glycol solution to be purified correspond to the general formula $HO(C_nH_{2n}O)_p$—$C_nH_2OH$, where n is an integer ranging from 2 to 4, and p represents 0 or an integer ranging from 1 to 4.

4. A process according to claim 1, wherein the glycol or glycols present in the glycol solution to be purified are selected from the group consisting of monoethylene glycol (MEG), diethylene glycol (DEG), triethylene glycol (TEG) and propylene glycol.

5. A process according to claim 1, the amount of water which is added to the glycol solution to be purified, in order to obtain demixing of the mixture into the hydrocarbon phase and the glycol phase, is such that the quotient $\alpha$ of the water:hydrocarbons volume ratio, in the glycol solution after addition of the water required for demixing, to the water:hydrocarbons volume ratio, in the glycol solution to be purified before addition of the water for demixing, is between 1 and 15.

6. A process according to claim 5, wherein the glycol solution to be purified is based on MEG and/or DEG and wherein d is $1<\alpha<2$.

7. A process according to claim 5, wherein the glycol solution to be purified is based on TEG and that $\alpha$ is such that $5<\alpha<10$.

8. A process according to claim 1 the addition of water to the glycol solution to be purified, resulting in demixing of the resulting mixture into the hydrocarbon phase and the glycol phase, and the separation of the said phases are performed at temperatures below about 60° C.

9. A process according to claim 1 the glycol phase arising from the demixing is subjected to a filtration before being brought to the desalting treatment, in order to remove solid particles whose mean diameter is greater than about 10 $\mu$m.

10. A process according to claim 1 the treatment for desalting the substantially hydrocarbon-free glycol phase is performed by percolation of the glycol solution to be desalted through one or more beds of ion exchange materials which selectively bind the anions or the cations respectively.

11. A process according to one of claims 1 to 9 characterized in that the treatment for desalting the substantially hydrocarbon-free glycol phase is performed by electrodialysis through membranes which are alternately selectively permeable to anions and to cations.

12. A process according to claim 1 the glycol solution arising from the desalting treatment is subjected to concentration by stripping using steam and optionally an extra gas.

13. A process according to claim 12, wherein the steps of demixing, desalting and concentration are performed continuously.

14. A process according to claim 12, wherein the steps of demixing and of concentration are performed continuously and the step of desalting is carried out intermittently.

15. A process according to claim 13, wherein desalting is performed by electrodialysis carried out with a DC electric current of constant intensity I and such that the current density, that is to say the ratio of the intensity I to the surface area of one of the electrodialysis membranes, is between 0.1 and 450 A/m$^2$.

16. A process according to claim 14, wherein the desalting is performed by electrodialysis carried out with a DC electric current, for which the mean value Im of the intensity, over the duration of the treatment, is such that the current density, that is wherein the ratio of the mean intensity Im to the surface area of one of the electrodialysis membranes, is between 0.1 and 450 A/m$^2$.

17. A process according to claims 15 or 16, wherein the glycol phase to be desalted contains a glycol consisting respectively of MEG, DEG and TEG and wherein the electrodialysis is performed with a current density between 0.1 and 150 A/m$^2$, 0.1 and 300 A/m$^2$ and 0.1 and 450 A/m$^2$ respectively.

18. A process according to claim 1 the glycol solution to be purified arises from the treatment of petroleum or gas production effluents by glycols.

19. A process according to claim 1 the glycol solution to be purified arises from the treatment, by glycols, for prevention of the formation of gas hydrates in the discharge pipes of multiphase effluents from petroleum or gas production.

20. A process according to claim 1, characterized in that the glycol solution to be purified is a used glycol solution arising from the treatment for dehydration of natural gases by glycols or a regenerated glycol solution arising from the concentration by stripping, using steam and optionally an extra gas, of such a used glycol solution.

21. The process according to claim 3 wherein the glycol possesses less than 7 carbon atoms in the molecule.

22. The process according to claim 5 wherein the quotient $\alpha$ is between 1 and 10.

* * * * *

UNITED STATES PATENT AND TRADEMARK OFFICE
CERTIFICATE OF CORRECTION

PATENT NO. : 5,817,889
DATED : October 6, 1998
INVENTOR(S) : Chantal Pondebat, Claude Blanc and Daniel Morin It is certified that error appears in the above-identified patent and that said Letters Patent is hereby corrected as shown below:

Column 2, line 54: the number of the U.S. Patent should read 4,427,507;

Column 11, Table I: the last value in the column entitled "Water" should be "1.015" instead of "3.015" and in the column entitled "Salts" the value ">0.01" should be "<0.01";

In the Claims:

Claim 3: the last part of the formula should read "-$C_nH_{2n}OH$";

Claims 5, 8, 9, 12 and 18-20: after "Claim 1", the first line insert --wherein--;

UNITED STATES PATENT AND TRADEMARK OFFICE
CERTIFICATE OF CORRECTION

PATENT NO. : 5,817,889
DATED : October 6, 1998
INVENTOR(S) : Chantel Pondebat, Claude Blanc and Daniel Morin It is certified that error appears in the above-identified patent and that said Letters Patent is hereby corrected as shown below:

Claim 6, last line: delete "d is";

Claim 11: revise the two first lines to read "A process according to Claim 1, wherein the treatment...";

Claim 16, line 5: delete the word "wherein";

Claim 11 and 20: delete "characterized in that" and insert --wherein--.

Signed and Sealed this

Second Day of March, 1999

Attest:

Q. TODD DICKINSON

*Attesting Officer*     *Acting Commissioner of Patents and Trademarks*